(12) United States Patent
Rich

(10) Patent No.: US 7,843,561 B2
(45) Date of Patent: Nov. 30, 2010

(54) OPTICAL SYSTEM FOR A FLOW CYTOMETER WITH AN INTERROGATION ZONE

(75) Inventor: Collin A. Rich, Ypsilanti, MI (US)

(73) Assignee: Accuri Cytometers, Inc., Ann Arbor, MI (US)

( * ) Notice: Subject to any disclaimer, the term of this patent is extended or adjusted under 35 U.S.C. 154(b) by 124 days.

(21) Appl. No.: 12/337,517

(22) Filed: Dec. 17, 2008

(65) Prior Publication Data

US 2009/0174881 A1 Jul. 9, 2009

Related U.S. Application Data

(60) Provisional application No. 61/014,376, filed on Dec. 17, 2007.

(51) Int. Cl.
*G01N 1/10* (2006.01)
(52) U.S. Cl. ........................................ 356/246; 356/73
(58) Field of Classification Search ................ 356/244, 356/246, 73, 432–440, 335–343, 39
See application file for complete search history.

(56) References Cited

U.S. PATENT DOCUMENTS

| | | | |
|---|---|---|---|
| 4,826,660 A | 5/1989 | Smith |
| 5,028,127 A | 7/1991 | Spitzberg |
| 5,139,609 A | 8/1992 | Fields et al. |
| 5,367,474 A | 11/1994 | Auer |
| 5,739,902 A | 4/1998 | Gjelsnes et al. |
| 5,798,222 A | 8/1998 | Goix |
| 6,016,376 A | 1/2000 | Ghaemi et al. |
| 6,091,502 A | 7/2000 | Weigl et al. |
| 6,097,485 A | 8/2000 | Lievan |
| 6,154,276 A | 11/2000 | Mariella, Jr. |
| 6,377,721 B1 | 4/2002 | Walt et al. |
| 6,403,378 B1 | 6/2002 | Phi-Wilson et al. |
| 6,469,787 B1 | 10/2002 | Meyer et al. |
| 6,519,355 B2 | 2/2003 | Nelson |
| 6,522,775 B2 | 2/2003 | Nelson |
| 6,636,623 B2 | 10/2003 | Nelson et al. |
| 6,700,130 B2 | 3/2004 | Fritz |
| 6,710,871 B1 | 3/2004 | Goix |
| 6,816,257 B2 | 11/2004 | Goix |
| 6,859,570 B2 | 2/2005 | Walt et al. |
| 6,869,569 B2 | 3/2005 | Kramer |
| 6,897,954 B2 | 5/2005 | Bishop |
| 6,936,828 B2 | 8/2005 | Saccomanno |
| 6,944,322 B2 | 9/2005 | Johnson et al. |
| 7,009,189 B2 | 3/2006 | Saccomanno |

(Continued)

FOREIGN PATENT DOCUMENTS

WO 2005/073694 1/2005

(Continued)

*Primary Examiner*—Hoa Q Pham
(74) *Attorney, Agent, or Firm*—Jeffrey Schox

(57) ABSTRACT

The optical system of the preferred embodiments includes a first light source that creates a first beam of a first wavelength, a first collimating element that collimates the first beam, a second light source 102 that creates a second beam of a second wavelength, a second collimating element that collimates the second beam, a beam combining element that combines the collimated beams, and a focusing element that focuses the combined collimated beam to a single point.

19 Claims, 2 Drawing Sheets

U.S. PATENT DOCUMENTS

| | | | |
|---|---|---|---|
| 7,012,689 B2 | 3/2006 | Sharpe | |
| 7,075,647 B2 | 7/2006 | Christodoulou | |
| 7,106,442 B2 | 9/2006 | Silcott | |
| 7,113,266 B1 | 9/2006 | Wells | |
| 7,232,687 B2 | 6/2007 | Lary et al. | |
| 7,262,838 B2 | 8/2007 | Fritz | |
| 7,362,432 B2 | 4/2008 | Roth | |
| 2002/0028434 A1 | 3/2002 | Goix | |
| 2003/0048539 A1 | 3/2003 | Oostman, Jr. et al. | |
| 2004/0048362 A1* | 3/2004 | Trulson et al. | 435/287.2 |
| 2004/0175837 A1 | 9/2004 | Bonne et al. | |
| 2004/0201845 A1 | 10/2004 | Quist et al. | |
| 2005/0047292 A1* | 3/2005 | Park et al. | 369/44.37 |
| 2005/0057749 A1 | 3/2005 | Dietz et al. | |
| 2005/0078299 A1* | 4/2005 | Fritz et al. | 356/39 |
| 2005/0105091 A1* | 5/2005 | Lieberman et al. | 356/369 |
| 2005/0162648 A1 | 7/2005 | Auer et al. | |
| 2005/0163663 A1 | 7/2005 | Martino et al. | |
| 2005/0195605 A1 | 9/2005 | Saccomanno et al. | |
| 2006/0023219 A1 | 2/2006 | Myer et al. | |
| 2006/0281143 A1 | 3/2006 | Liu et al. | |
| 2007/0041013 A1 | 2/2007 | Fritz et al. | |
| 2007/0096039 A1* | 5/2007 | Kapoor et al. | 250/458.1 |
| 2010/0118298 A1 | 5/2010 | Bair et al. | |

FOREIGN PATENT DOCUMENTS

| | | |
|---|---|---|
| WO | WO/2005/017499 | 2/2005 |
| WO | WO/2005/073694 | 8/2005 |

* cited by examiner

OPTICAL SYSTEM FOR A FLOW CYTOMETER WITH AN INTERROGATION ZONE

CROSS-REFERENCE TO RELATED APPLICATIONS

This application claims the benefit of US Provisional Application No. 61/014,376 filed 17 Dec. 2007, which is incorporated in its entirety by this reference.

TECHNICAL FIELD

This invention relates generally to the flow cytometer field, and more specifically to a new and useful optical system in the flow cytometry field.

BACKGROUND

The conventional optical system for flow cytometers requires aligning the light sources in relation to the lenses to shine multiple frequencies of light on a sample simultaneously. Since the light source affects the detection of each of the detector subsystems, this alignment must be precise or the performance of the system is dramatically reduced. To achieve this precision, however, requires expensive manufacturing techniques and/or time-consuming manual alignment. Thus, there is a need in the flow cytometer field to create a new and useful optical system. This invention provides such new and useful optical system.

DESCRIPTION OF THE PREFERRED EMBODIMENTS

The following description of the preferred embodiments of the invention is not intended to limit the invention to these preferred embodiments, but rather to enable any person skilled in the art to make and use this invention.

Figure 1:
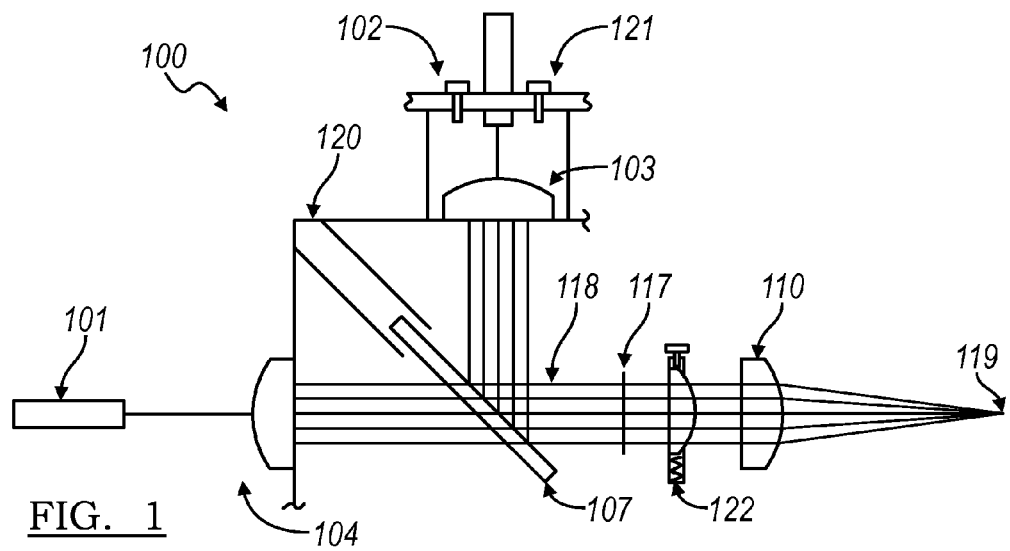
FIG. 1 is a schematic representation of a first preferred embodiment of the invention.

As shown in FIG. 1, the optical system of the preferred embodiments includes a first light source 101 that creates a first beam of a first wavelength, a first collimating element 103 that collimates the first beam, a second light source 102 that creates a second beam of a second wavelength, which is different than the first wavelength, a second collimating element 104 that collimates the second beam, a beam combining element 107 that combines the collimated beams of the first and second collimating elements to form a combined collimated beam that is multichromatic, and a focusing element 110 that focuses the combined collimated beam to a single point. The optical system 100 was specifically designed to focus a multichromatic beam at a single point in an interrogation zone of a flow cytometer, but may alternatively be used in any suitable device or system. The optical system 100 overcomes the disadvantages of the conventional optical systems for flow cytometers because, even if the light sources are not perfectly aligned with each other (or the beam combing element 107), enough light from the light sources will be combined to form an adequate multichromatic beam.

The light sources 101 and 102, which are preferably mounted to the base, function as two independent light sources. The light sources 101 and 102 are preferably lasers of different light frequencies. The first light source 101 is preferably a blue laser and the second light source 102 is preferably a red laser, but the light sources 101 and 102 may alternatively be any two different light sources that vary in wavelength, frequency, phase, polarization, light signal, and/or any suitable light characteristic. The light sources 101 and 102 may additionally be generated from a laser diode and/or any suitable optical setup to generate a suitable light source. In an alternative embodiment, the system 100 may further include a third light source (not shown) that produces a third beam with yet another light characteristic.

The collimating elements 103 and 104 function to collimate light from the light sources 101 and 102, respectively. The collimated elements 103 and 104 preferably convert light into a collimated beam where light energy is uniformly (or near uniformly) distributed across a larger area. The collimated beam may alternatively have a gradient of light energy, a Gaussian distribution, or any suitable beam parameter of distributed light energy. The collimated beam preferably travels in a single direction and does not disperse radially outward from a point. The collimating element 103, which is preferably mounted to the first light source 101, is located between the first light source 101 and the beam combining element 107. The collimating element 104, which is preferably mounted to the second light source 102, is located between the second light sources 102 and the beam combining element 107. In one version, one or both of the collimating elements 103 and 104 may be combined or integrated with the light sources 101 and 102, such that each light source 101 and 102 produces collimated light. In another version, one or both of the collimating elements 103 and 104 may be fastened to, or otherwise optically communicating with, the light sources 101 and 102. The collimating elements 103 and 104 are preferably conventional collimating lens, but may alternatively be any suitable device to collimate the beams from the light sources 101 and 102.

The beam combining element 107, which is preferably mounted to the base, functions to combine the collimated beams from the light sources 101 and 102. The light between the beam combining element 107 and the focusing element 110 is preferably a collimated beam. Additionally, the light entering the beam combining element 107 is preferably a collimated beam (or beams). The collimated beam functions to reduce the tolerances and/or difficulty of optical alignment and manufacturing tolerances of the optical system. The loss of light due to minor misalignment (where at least a designated minimum percentage of light hits a target) is preferably allowable due to the light being a collimated beam. A collimated beam is preferably used to traverse the longer distances of the optical system. In a first version, the beam combining element 107 is a conventional beam splitter. The beam splitter is preferably selectively transmissive and preferably allows the light of an appropriate bandwidth from at least one light source to pass through it, and the beam splitter is also preferably reflective to allow at least one other light source to be reflected from it. Preferably, the collimated light from at least one light source 102 passes through the beam splitter 107, while collimated light from at least one other light source 101 is reflected off the other side of the beam splitter 107, to create multichromatic collimated beams 118. In other versions, the beam combining element 107 may include beam combiners, mirrors, optical prisms, fiber optics, and/or any suitable device or method to combine the beams from the light sources 101 and 102.

Figure 2:
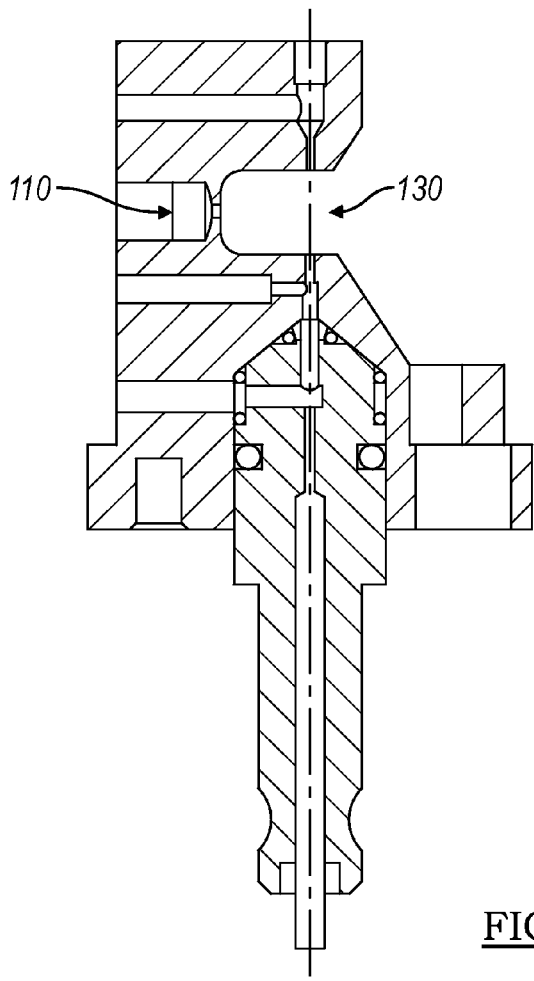
FIG. 2 is a cross-sectional view of a flow cell of the preferred embodiment of the invention.
Figure 3:
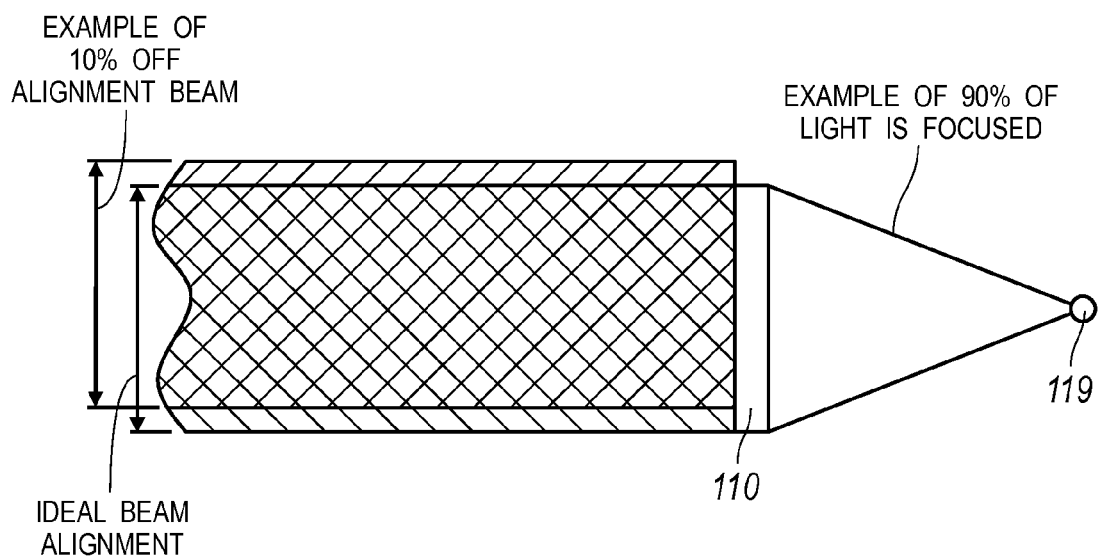
FIG. 3 is a detailed schematic representation of a collimated beam that is incident on a focusing element of the preferred embodiment of the invention.

The focusing element 110 functions to focus the multichromatic collimated beams 118 to a single point. The focusing element 110 is preferably an achromatic lens, but may also be multiple lenses and/or lens configurations or any other suitable focusing element. The focusing element 110 is preferably positioned such that the light is focused on the interrogation zone 119 of the flow cytometer. As shown in FIG. 3, the focusing element preferably allows for slight misalignment of the multichromatic collimated beam. The focusing element may additionally allow for slight misalignment of the first light source 101 with respect to the collimated light from the second light source 102. The focusing element preferably has a target area on the focusing element where incident light is focused on the interrogation zone 119. The target area is preferably suitably large (e.g. magnitude of a collimated beam width) to allow for variation and small errors in optical alignment. The light energy of the multichromatic collimated beam is preferably distributed over the area of the collimated beam cross-section such that a majority or sufficient amount of light energy is incident on the target area. For example, a multichromatic collimated beam may be misaligned by 10% but the focusing element 110 is preferably able to focus 90% of the light (the part that is incident on the target area) on the interrogation zone and this is preferably sufficient. The target area is preferably uniform in focusing capability but may alternatively have a distribution of focusing capability, or any suitable mapping of focusing capability and may be any suitable shape or size. In a first version, as shown in FIG. 2, the focusing element 110 is preferably mounted to a flow cell 130 of a flow cytometer. The flow cell 130 is preferably similar to the one disclosed in PCT Application number US2007/83991 filed 7 Nov. 2007, which is incorporated in its entirety by this reference, but may alternatively be any suitable interrogation zone 119 of a flow cytometer. The light within the flow cell 130 (the light from the focusing element 110) is preferably an uncollimated (or focused) beam. The flow cell 130 is preferably manufactured and/or controlled with tight dimensional and optical tolerances such that precise optical alignment is achieved within the flow cell 130. Additionally, the distance the laser light travels is preferably minimized to reduce the likelihood of misalignment. In a second version, the focusing element 110 may be mounted, either directly or indirectly, to the beam combining element 107, a bracket 120, and/or to a base.

In one variation, the optical system 100 includes a removable filter 117 that functions to filter the multichromatic collimated beams 118 from the beamsplitter 107. The filter 117 is preferably removable, replaceable, tunable, or variable in some fashion by the user of the system and/or by a central processor. Alternatively, the filter may also be a coating on a beamsplitter 107, and/or a coating on the focusing element 110. The removable filter 117 may alternatively filter light from the first light source 101 and/or second light source 102. Additionally, a plurality of filters may alternatively be used to filter light during multiple suitable stage of the optical system. The filter 117 functions to absorb spurious emissions and/or to "clean up" the light. The optical system 100 may, however, omit the removable filter or may include a filter and/or filters that are not variable.

In another variation, the optical system 100 includes a bracket 120 that functions to align and hold the light sources 101 and 102, the collimating elements 103 and 104, and the beam splitter 107 in the correct positions to produce collimated multichromatic light. The bracket 120 is preferably mounted to a base or surface of a flow cytometer. The bracket 120 preferably achieves alignment of the optical system once the bracket 120 is mounted. Additionally, minor adjustments to components of the optical system may be needed to optimize the optical system. The bracket 120 may alternatively include an adjustable mount for at least one of the light sources 101 and 102. The adjustable mount 121 is preferably adjustable along two axis and functions to allow the second light source 102 to be aligned with the first light source 101. The adjustable mount 121 preferably has a resolution of adjustment that enables alignment of the second light source, such that at least some minimum amount of light is positioned for the focusing element 110. For example, the adjustment mount may allow for at least 90% of the collimated light to be acceptably focused onto the interrogation zone 119. The resolution is preferably achieved through and/or takes into account component manufacturing tolerances, mechanism design, system dimension variance and/or system specification (e.g. allowable vibration tolerances and temperature tolerances). The optical system 100 may, however, omit the bracket 120 and use other techniques to align the elements of the system.

In another version, the optical system 100 includes a vertical lens 122 that functions to align the multichromatic collimated beam with the interrogation zone of the flow cytometer. The vertical lens 122 is preferably adjustable along an axis perpendicular to the path of the multichromatic collimated beam. Additionally, the adjustment axis is preferably perpendicular to the flow channel of the flow cytometer. The vertical lens 122 is preferably adjusted by turning a setscrew or alternatively any suitable mechanism may be used. The vertical lens 122 preferably has a resolution of adjustment that enables the multichromatic collimated beam to be aligned along one axis, such that at least some minimum amount of light is positioned for the focusing element 110. For example, the adjustment resolution may ensure that at least 90% of the collimated light can be acceptably focused onto the interrogation zone 119. The resolution of the vertical lens adjustment is preferably achieved through and/or takes into account component manufacturing tolerances, mechanism design, system dimension variance and/or system specification (e.g. allowable shock tolerances and temperature tolerances) The vertical lens 122 may additionally be designed to work in cooperation with the adjustable mount 121. In this additional alternative, the adjustable mount 121 and vertical lens 122 preferably adjust the multichromatic collimated beam to focus at least some minimum amount into the interrogation zone 119. The optical system 100 may, however omit the vertical lens 122 or may include any other suitable device to provide a similar functionality.

In yet another version, the optical system 100 includes a base that functions to support and align the elements of the system. In one variation, the light sources 101 and 102, the beam combining element 107 (or the bracket 120), and the flow cell 130 are all individually mounted to the base. In another variation, the light sources 101 and 102, the beam combining element 107 (or the bracket 120), and the focusing element 100 are all individually mounted to the base. The base is preferably made of a rigid material, such as steel, but may alternatively be made of any suitable material that provides support and alignment to the elements of the system.

As a person skilled in the art will recognize from the previous detailed description and from the figures and claims, modifications and changes can be made to the preferred embodiments of the invention without departing from the scope of this invention defined in the following claims.

I claim:

1. An optical system for a flow cytometer with an interrogation zone, the system comprising:
   a first light source that creates a first beam of a first wavelength;
   a first collimating element that collimates the first beam;
   a second light source that creates a second beam of a second wavelength, which is different than the first wavelength;
   a second collimating element that collimates the second beam from the second light source;
   a beam combining element that combines the collimated beams of the first and second collimating elements to form a combined collimated beam that is multichromatic,
   a focusing element that focuses the combined collimated beam to a single point; and
   a bracket including an adjustable mount for at least one of the first and the second light sources that allows for alignment of the second light source relative to the first light source, wherein the adjustable mount is adjustable along two axes.

2. The optical system of claim 1 wherein the first light source is a blue laser and the second light source is a red laser.

3. The optical system of claim 2 wherein the red laser is produced by a red laser diode.

4. The optical system of claim 1 wherein the single point is located in the interrogation zone of the flow cytometer.

5. The optical system of claim 4 wherein the focusing element is located on a flow cell of the flow cytometer.

6. The optical system of claim 5 wherein the light between the beam combining element and the focusing element is a collimated beam, and wherein the light within the flow cell is focused light.

7. The optical system of claim 6 wherein the beam combining element is a beam splitter.

8. The optical system of claim 7 wherein the focusing element focuses a portion of a collimated beam on the single point when a collimated beam is partially incident on the focusing element.

9. The optical system of claim 4 further comprising a flow cell that defines the interrogation zone for the flow cytometer, wherein the focusing element is located on the flow cell.

10. The optical system of claim 9 wherein the light between the beam combining element and the focusing element is a collimated beam, and wherein the light within the flow cell is focused light.

11. The optical system of claim 10 wherein the beam combining element is a beam splitter.

12. The optical system of claim 10 wherein the focusing element focuses a portion of a collimated beam on the single point when a collimated beam is partially incident on the focusing element.

13. The optical system of claim 12 further including an adjustable vertical lens positioned between the beam combining element and the flow cell, wherein the lens modifies the position of the combined collimated beam.

14. The optical system of claim 13 further including a changeable optical filter.

15. The optical system of claim 1 further including an adjustable vertical lens positioned between the beam splitter and the flow cell, wherein the lens modifies the position of the combined collimated beam.

16. The optical system of claim 15 further including a changeable optical filter.

17. The optical system of claim 1 further comprising a base, wherein the first light source, the second light source, and the beam combining element are mounted to the base.

18. The optical system of claim 17 wherein the first collimating element is mounted to the first light source, and wherein the second collimating element is mounted to the second light source.

19. The optical system of claim 17 further comprising a flow cell that defines the interrogation zone for the flow cytometer, wherein the focusing element is located on the flow cell, and wherein the flow cell is mounted to the base.

* * * * *